(12) United States Patent
Khanuja et al.

(10) Patent No.: US 6,660,761 B2
(45) Date of Patent: Dec. 9, 2003

(54) METHOD OF TREATMENT FOR FUNGAL INFECTIONS WITH A SYNERGISTIC FORMULATION OF ANTIFUNGAL AGENTS

(75) Inventors: Suman Preet Singh Khanuja, Lucknow (IN); Puspalata Chatruvedi, Lucknow (IN); Krishna Kumar Agarwal, Lucknow (IN); Atique Ahmad, Lucknow (IN); Tiruppadiripuliyur Ranganathan Santha Kumar, Lucknow (IN); Mahendra Pandurang Darokar, Lucknow (IN); Ajit Kumar Shasany, Lucknow (IN); Jai Shankar Arya, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/066,802

(22) Filed: Feb. 6, 2002

(65) Prior Publication Data
US 2003/0158126 A1 Aug. 21, 2003

(51) Int. Cl.$^7$ ............... A61K 31/4174; A61K 31/7036

(52) U.S. Cl. .......................................... 514/396; 514/31
(58) Field of Search ................... 514/31, 396

(56) References Cited

U.S. PATENT DOCUMENTS

2002/0176827 A1 * 11/2002 Rajaiah et al. ................ 424/49

* cited by examiner

Primary Examiner—Phyllis G. Spivack
(74) Attorney, Agent, or Firm—Crowell & Moring LLP

(57) ABSTRACT

The present invention relates to a method of treatment of fungal infections consisting essentially of a synergistic combination of plant compounds that are useful for enhancing the activity of antifungal compounds. The plant compounds, menthol and menthyl acetate, when mixed at specific concentrations, enhance the antifungal activity of the commercially available fungicides.

18 Claims, No Drawings

METHOD OF TREATMENT FOR FUNGAL INFECTIONS WITH A SYNERGISTIC FORMULATION OF ANTIFUNGAL AGENTS

FIELD OF INVENTION

The invention relates to a method of treatment for fungal infection with synergistic combination of plant compounds useful for enhancing the activity of antifungal compounds. The plant compounds menthol and menthyl acetate when mixed at specific concentrations enhances the antifungal activity of the commercially available fungicides.

BACKGROUND OF THE INVENTION

In spite of tremendous advances made in the modem system of medicine there are still large number of diseases for which suitable drugs are still not available in the modern system of medicine. Areas where new drugs are urgently needed include tropical diseases like bacterial and viral infections, rheumatism and immuno-modulators. Out of many diseases, skin infections caused by fungal pathogens are very common especially in tropical, under-developed and in developing countries due to poor hygienic conditions. Fungal infections of the skin are very common in all age groups. They are caused by microscopic fungal organisms, which normally live on the skin surface without causing symptoms. Under appropriate conditions of moisture, warmth, irritation, or minor skin injury, they start to grow more rapidly and invasively, causing a range of health problems. Tropical environment where the heat and humidity allow the fungi to thrive is yet another important factor in the spread of fungal diseases. Infection also occurs when the body is exposed to pathogens or organisms that are usually non-pathogenic but become a threat for reasons such as on account of decrease in immune systems mainly because of organ transplant operations, cancer chemotherapy and acquired immune deficiency syndrome (AIDS).

To counter these infections only a handful of antifungal agents such as Greseofulvine, Amphotericin, Nystatin and Azole derivatives are available in the market. Most of these antifungals are synthetic derivatives with known serious side effects and toxicity to human and animals. Compounding this problem is the development of resistance towards commonly used drugs thus rendering the chemotherapy less useful. Therefore new antifungal substances from natural sources have to be generated to counter the resistance phenomenon.

Superficial fungal infections of skin affect millions of people throughout the world. Most of these skin diseases are caused by dermatophytic fungi like *Trichophyton rubrum Trichophyton mentagrophytes Microsporum gypseum Epidermophyton floccossum* and *Candida albicans*, which are infectious in nature. Secondary infections due to bacteria are common in the primary skin lesions. In India, large number of people are involved in agriculture with majority of them living in villages where due to the prevailing unhygienic conditions, the incidence of mycotic infections are severe. Moreover, the skin infections spread rapidly due to poor hygienic conditions, increase in the density of the population and increase in the level of environmental pollution. Medicinal plants have been playing an important role in world health as 80% of the world population rely chiefly on traditional medicines for their primary health care (WHO, 1993). Use of plant derived drugs has an added advantage of being 'natural' with little side effects or toxicity. It is well known that the plant-derived products are extensively used as biologically active compounds. Among them essential oils, where the first preservative used by man, originally in their natural state within plant tissues then as oils obtained by distillation mainly because of their anti-microbial properties and pleasant odour. Many of the essential oils have found to have antifungal, cytostatic and insecticidal activities (Franzias et al. 1997). Because of their notable antimicrobial activity coupled with pleasing flavour the essential oils can be used to treat microbial infections such as skin diseases.

Skin constitutes the major part of the exposed part in the body. Natural remedies have been the most accepted and are relatively the safer means for treating fungal diseases since they are less likely to interfere with the beauty and attraction of the skin. Plants being an important source of antimicrobial substances can be used effectively for the treatment of skin diseases. Beauticians and skin specialists are the first to realize the protective role of herbal products, as they are less toxic and believed to enhance the skin attractions.

The incidence of fungal infections is increasing alarmingly, due to reasons mentioned above. During 1990–96 the world market for antifungals is over U.S. $1500 millions representing 1.5% of the total global anti-infective market. Currently anti-fungals (both topical and systemic) represent more than 6% of the total anti-infective agents. The world market for antifungals is expanding at the rate of 20% per annum and is estimated to reach over U.S. $600 million/annum. However, many of the synthetic antifungals cause side effects in immune stressed individuals. On the other hand, plant products such as Echinaceae and tea tree not only helps cure infections but also boost the immune system. Therefore, formulations made out of herbal compounds will have more acceptances than the synthetic antifungals for applying in the external affected area (topical applications).

Candidiasis is a mycotic disease caused by a species of Candida usually *Candida albicans*, which affects man and animals. In man candidiasis commonly occurs as localized infections of the mouth (oral thrush), and vagina (vaginal thrush) and involves the formation of whitish mucoid plaques on the mucous membrane. Cutaneous candidiasis tend to occur on skin areas constantly exposed to moisture, regions commonly affected include eg., the groin and axillae. The infected skin is swollen, red and pruritic. Chronic muco-cutaneous candidiasis is a severe condition, which occurs, in immuno-compromised or otherwise abnormal individuals; the skin and mucous membranes of the entire body may be affected, with chronic, granulomatous, inflammatory reactions in the underlying tissues. Other forms of candidiasis include broncho-candidiasis, pulmonary candidiasis and systemic candidiasis.

Cryptococcosis is also a fungal disease of man and animals caused by *Cryptococcus neoformans*; infection occurs on inhalation of dust contaminated with the fungus. Pulmonary infection may be mild or inapparent. However, particularly in individuals with defective CMI or certain leukemia, the disease may become disseminated to almost any tissue (liver, bones, skin etc.) but especially to meninges leading to cryptococcal meningitis, which is often fatal.

Fungal infections such as candidiasis, cryptococcosis and dermatophytoses (ringworms) are mostly treated with antibiotics namely Griseofulvin, Amphotericin B, terbinafine and Azole compounds such as Clotrimazole, Flucanazole, Miconazole, Itracanazole, Ketoconazole etc. However, all these antifungals exhibit serious side effects to humans limiting their clinical usefulness.

Combinations of antimicrobial agents are generally used for one of the following purposes: (i) to increase the fungicidal activity and/or the rate of killing in vivo, (ii) to prevent the emergence of drug resistance, or (iii) to enlarge the antimicrobial spectrum for curing poly-microbial infections. Synergism can be defined as the fungicidal activity of the drug combination significantly more pronounced than the sum of the fungicidal effect of each agent alone in comparison with the effect in untreated control (Fantin B and Carbon C, 1992, *Antimicrobial Agents and Chemotherapy* 36 (5): 907–912).

In the present invention Candida albicans (MTCC1637 equivalent to ATCC is 18804)=Interdigital mycoses; Neo-type strain, production of citric acid) is used for all the experimentations (MTCC=Microbial type culture collection, Institute of Microbial Technology, Chandigarh, India).

Planned experiments are carried out to test the synergism between plant compounds/compound combinations and the commercially available anti-fungals like Clotrimazole, Amphotericin B and Nystatin. Out of all the combinations, the combination of Menthol and menthyl acetate in specific ratios is found to be synergistically increasing the activity of the anti-fungal compounds.

The compound Menthyl acetate is a liquid and 99.2% pure as analyzed through GLC. This is a well-characterized compound and is obtained from the chemistry division of Central Institute of Medicinal and Aromatic Plants (CIMAP), Lucknow, India. The compound menthol is procured from Sigma chemical company, USA.

OBJECTS OF THE PRESENT INVENTION

The main object of the present invention is to provide a method of treatment for fungal infection by effectively using natural plant compounds, which can enhance the bioactivity of antifungals.

Another object of the invention is to reduce the concentration of these antifungals to a level/dosage at which they do not exhibit any side effects and hence safe to use. Yet another object of the present invention is to screen a large number of plant compounds and their combinations for synergism with the antifungals like Clotrimazole, Amphotericin B and Nystatin due to the plant origin and lower concentrations in which used are non-toxic.

SUMMARY OF THE INVENTION

The present invention relates to a method of treatment of fungal infection with a combination of plant compounds synergistically acting to increase the activity of antifungal compounds. The compounds are Menthol and Menthyl acetate which when mixed at specific concentrations improves the antifungal activity of the commercially available fungicides which is higher than simple addition in the individual activities.

DETAILED DESCRIPTION OF THE PRESENT INVENTION

Accordingly, the present invention provides a method of treating fungal infection with a bioactive synergistic formulation comprising the following ingredients:

(a) menthol in the range of 1–54%;
(b) menthyl acetate in the range of 1.5–62%; and
(c) an antifungal compound in the range of 23–95%.

In an embodiment of the present invention, the concentration of antifungal compounds is in the range of 0.078–5.0 µg/ml.

In yet another embodiment of the present invention, the antifungal compounds are selected from the group consisting of Clotrimazole, Amphotericin B and Nystatin.

In another embodiment of the present invention, the concentration of Clotrimazole in the formulation is in the range of 0.078–0.3125 µg/ml.

In still another embodiment of the present invention, the concentration of Amphoterecin B in the formulation is in the range of 0.15625–1.25 µg/ml.

In yet another embodiment of the present invention, the concentration of Nystatin in the formulation is in the range of 0.15625–5 µg/ml.

In still another embodiment of the present invention, the most preferred concentration each of menthol and menthyl acetate in the formulation is 0.125 µg/ml respectively.

In yet another embodiment of the present invention, the ratio of menthol and menthyl acetate is in the range of 0.05–3.2.

In still another embodiment of the present invention, the ratio of menthol and menthyl acetate with Clotrimazole is in the range of 0.80–3.2.

In yet another embodiment of the present invention, the ratio of menthol and menthyl acetate with Amphotericin is in the range of 0.20–1.6.

In still another embodiment of the present invention, the ratio of menthol and menthyl acetate with Nystatin is in the range of 0.05–1.6.

In yet another embodiment of the present invention, the enhanced activity of the formulation is in the range 16 to 32 fold over the antifungal agents used in isolation.

In still another embodiment of the present invention, said formulation consisting of menthol having a specific gravity of 0.981 and the purity to the extent of 99.0%, is dissolved in menthyl acetate having a specific gravity 0.92 and the purity of 99.2%.

In another embodiment of the present invention, said formulation is used to treat human beings.

In yet another embodiment of the present invention, said formulation is effective against pathogens selected from group consisting of cryptococcosis, dermatophytoses and preferably *Candida albicans*.

In still another embodiment of the present invention, the formulation is administered in the form of oral, topical preparations and by other pharmaceutically accepted methods.

In yet another embodiment of the present invention, the formulation is effective in preventing the drug resistance.

In still another embodiment of the present invention, the formulation is effective in curing polymicrobial infections.

The present invention is further explained in the form of following examples. These examples however should not be construed to limit the scope of the invention.

Planned experiments are carried out to test the synergism between plant compounds/compound combinations and the commercially available anti-fungals like Clotrimazole, Amphotericin B and Nystatin.

EXAMPLE 1

The minimum inhibitory concentrations (MIC) of the compound menthyl acetate and menthol is determined in broth culture of *Candida albicans* and is estimated to be 1/400 and 500 µg/ml respectively.

EXAMPLE 2

A combination of the two compounds menthol and menthyl acetate in 1:1 ratio is evaluated for synergistic action if any. It is found that the combination had much higher activity leading to a MIC of 1/1600 against *Candida albicans*. Therefore this combination is further tested for activity against Candida in combination with known antifungal drugs.

EXAMPLE 3

The combination of menthol and menthyl acetate (1:1) is tested for synergism with antifungal agents like Clotrimazole, Amphotericin B and Nystatin in the following combinations.

| Antifungal agent | Concentration (μg/ml) | | Menthol + Menthyl acetate (μg/ml) | |
|---|---|---|---|---|
| | Minimum | Maximum | Minimum | Maximum |
| Clotrimazole | 0.5 | 5.0 | 0.125 | 10.0 |
| Amphotericin B | 10.0 | 20.0 | 0.125 | 10.0 |
| Nystatin | 0.5 | 6.0 | 0.125 | 10.0 |

It is observed that menthol, menthyl acetate combination is most effective in synergizing the activity of these three anti-fungal agents at 0.25(μg/ml) concentration. Now to work out various ratios of menthol and menthyl acetate at this concentration with these antifungal agents detailed experiments are carried out.

EXAMPLE 4

Following ratios are prepared by dissolving menthol in menthyl acetate. The ratios are tested for minimum inhibitory concentration in broth cultures of *Candida albicans*. As mentioned in the TABLE 1, the MIC of ratios are several folds lower than the additive MIC of individual compounds. Identification numbers of the ratios are the numbers given to identify the combination and mean nothing more than this. The most effective combination is 2115 (1/3200 dilution), followed by 2113, 2114, 2116 (1/1600 dilution) and 211, 2112 (1/800 dilution). All these combinations are found to be synergistic for antifungal activities.

TABLE 1

| Identification number of the ratio | Menthol (g) | Menthyl acetete (g) | MIC of the ratios against *Candida albicans* |
|---|---|---|---|
| 2111 | 20 | 80 | 1/800 |
| 2112 | 30 | 70 | 1/800 |
| 2113 | 40 | 60 | 1/1600 |
| 2114 | 50 | 50 | 1/1600 |
| 2115 | 60 | 40 | 1/3200 |
| 2116 | 70 | 30 | 1/1600 |

EXAMPLE 5

The individual compounds menthol and menthyl acetate, at MIC concentrations are tested for synergism with the antifungal compounds Clotrimazole, Amphotericin B and Nystatin and it is found that neither menthol nor menthyl acetate could lower the MIC of these compounds in such combinations at a concentration of 0.25 μg/ml. (TABLE 2).

TABLE 2

| Clotrimazole (C) + Menthol(μg/ml) | MIC (μg/ml) | Fold increase | Clotrimazole (C) + Menthyl acetatel(μg/ml) | MIC (μg/ml) | Fold increase |
|---|---|---|---|---|---|
| Clotrimazole (C) | 1.25 | — | Clotrimazole (C) | 1.25 | — |
| C + 0.05 | 1.25 | 1 | C + 0.20 | 1.25 | 1 |
| C + 0.075 | 1.25 | 1 | C + 0.175 | 1.25 | 1 |
| C + 0.10 | 1.25 | 1 | C + 0.15 | 1.25 | 1 |
| C + 0.125 | 1.25 | 1 | C + 0.125 | 1.25 | 1 |
| C + 0.150 | 1.25 | 1 | C + 0.10 | 1.25 | 1 |
| C + 0.175 | 1.25 | 1 | C + 0.075 | 1.25 | 1 |
| Amphotericin B(A) + Menthol(μg/ml) | MIC (μg/ml) | Fold increase | Amphotericin B (A) + Menthyl acetatel(μg/ml) | MIC (μg/ml) | Fold increase |
| Amphotericin B (A) | 2.5 | — | Amphotericin B (A) | 2.5 | — |
| A + 0.05 | 2.5 | 1 | A + 0.20 | 2.5 | 1 |
| A + 0.075 | 2.5 | 1 | A + 0.175 | 2.5 | 1 |
| A + 0.10 | 2.5 | 1 | A + 0.15 | 2.5 | 1 |
| A + 0.125 | 2.5 | 1 | A + 0.125 | 2.5 | 1 |
| A + 0.150 | 2.5 | 1 | A + 0.10 | 2.5 | 1 |
| A + 0.175 | 2.5 | 1 | A + 0.075 | 2.5 | 1 |
| Nystatin (N) + Menthol(μg/ml) | MIC (μg/ml) | Fold increase | Nystatin (N) + Menthyl acetatel(μg/ml) | MIC (μg/ml) | Fold increase |
| Nystatin (N) | 5.0 | — | Nystatin (N) | 5.0 | — |
| N + 0.05 | 5.0 | 1 | N + 0.20 | 5.0 | 1 |
| N + 0.075 | 5.0 | 1 | N + 0.175 | 5.0 | 1 |
| N + 0.10 | 5.0 | 1 | N + 0.15 | 5.0 | 1 |
| N + 0.125 | 5.0 | 1 | N + 0.125 | 5.0 | 1 |
| N + 0.150 | 5.0 | 1 | N + 0.10 | 5.0 | 1 |
| N + 0.175 | 5.0 | 1 | N + 0.075 | 5.0 | 1 |

EXAMPLE 6

The ratios of menthol and methyl acetate are tested for different concentrations, for enhanced activity of the antifungal compounds and a concentration of 0.25(μg/ml) is selected on the basis of potency and activities of enhancement at all the ratios tested. The fractional inhibitory concentrations (FIC) are calculated by dividing the MIC of the combination with the MIC of antifungal compound alone. The enhancement is calculated by dividing the MIC of the antifungal compound with the MIC of the combination. The ratios at a concentration much below the MIC in combination with Clotrimazole could enhance the activity of Clotrimazole 4 to 16 folds with the maximum enhancement activity for the three combinations 2114, 2115, and 2116. Similarly, the maximum enhancement of Amphotericin is detected for the same set of ratios (2114, 2115, 2116). The enhancement of Nystatin is detected in the combinations with ratios 2112 and 2114. (TABLE 3)

TABLE 3

Effect of combination of menthol and menthyl acetate with antifungal drugs against *Candida albicans*.

| Combinations | Conc. of combination used (μg/ml) | MIC (in μg/ml) | FIC(in μg/ml) | Fold enhancement (on the basis of reduction in the MIC level of antifungal drugs) |
|---|---|---|---|---|
| Clotrimazole in combination | | | | |
| Clotrimazole (C) | 0.00 | 1.25 | — | — |
| C + 2111 | 0.25 | 0.3125 | 0.25 | 4.0 |
| C + 2112 | 0.25 | 0.15625 | 0.125 | 8.0 |
| C + 2113 | 0.25 | 0.15625 | 0.125 | 8.0 |
| C + 2114 | 0.25 | 0.078 | 0.0625 | 16.0256 |
| C + 2115 | 0.25 | 0.078 | 0.0624 | 16.0256 |
| C + 2116 | 0.25 | 0.078 | 0.0624 | 16.0256 |
| Amphoterisin B in combinations | | | | |
| Amphotericin B (A) | 0.00 | 2.5 | — | — |
| A + 2111 | 0.25 | 1.25 | 0.5 | 2.0 |
| A + 2112 | 0.25 | 0.625 | 0.25 | 4.0 |
| A + 2113 | 0.25 | 1.25 | 0.5 | 2.0 |
| A + 2114 | 0.25 | 0.15625 | 0.0625 | 16.0 |
| A + 2115 | 0.25 | 0.15625 | 0.0625 | 16.0 |
| A + 2116 | 0.25 | 0.15625 | 0.0625 | 16.0 |
| Nystatin in combinations | | | | |
| Nystatin (N) | 0.00 | 5.0 | — | — |
| N + 2111 | 0.25 | 5.0 | 1.0 | 1.0 |
| N + 2112 | 0.25 | 0.15625 | 0.03125 | 32.0 |
| N + 2113 | 0.25 | 1.25 | .5 | 4.0 |
| N + 2114 | 0.25 | 0.15625 | 0.03125 | 32.0 |
| N + 2115 | 0.25 | 0.625 | 0.125 | 8.0 |
| N + 2116 | 0.25 | 0.3125 | 0.0625 | 16.0 |

From the illustrations above, the following has been observed (a) the concentration 2112 (30 g menthol+70 g menthyl acetate);

(b) the concentration 2113 (40 g menthol+60 g menthyl acetate);

(c) the concentration 2114 (50 g menthol+50 g menthyl acetate);

(d) the concentration 2115 (60 g menthol+40 g menthyl acetate);

(e) the concentration 2116 (70 g menthol+30 g menthyl acetate); and (f) enhance the activity of the antifungal compounds several folds.

On the basis of above inference, it is observed that when the combination of menthol (30 to 70 g) (specific gravity, 99.99% pure) is dissolved in menthyl acetate (30 to 70 g) (specific gravity 0.92, 99.2% pure) is used at a concentration of 0.025%, with the antifungal compounds, the activity of these compounds is enhanced to a maximum of 32 folds.

The ratios 2111, 2112, 2113, 2114, 2115, 2116 are found to be synergistically active by lowering the (Minimum Inhibitory Capacity) of the antifungal compound when used in the concentration of 1/5 times of the MIC Clotrimazole, 1/10 times of the MIC of Amphotericin, 1/20 times of the MIC of Nystatin.

Ratios of menthol and menthyl acetate used for Clotrimazole are provided in the Table 4

TABLE 4

| Ratios | Menthol (g): Menthyl acetate (ml) | Amount of the combinations to be used (μg/ml), (menthol, menthyl acetate(μg/ml)) | Amount of Clotrimazole (μg/ml) | Ratio of menthol and menthyl acetate combination to Clotrimazole | Fold enhancement |
|---|---|---|---|---|---|
| 2111 | 20:80 | 0.25 (0.05:0.20) | 0.3125 | 0.80 | 4.0 |
| 2112 | 30:70 | 0.25 (0.075, 0.175) | 0.15625 | 1.60 | 8.0 |
| 2113 | 40:60 | 0.25 (0.10, 0.15) | 0.15625 | 1.60 | 8.0 |
| 2114 | 50:50 | 0.25 (0.125, 0.125) | 0.078 | 3.20 | 16.0256 |
| 2115 | 60:40 | 0.25 (0.15, 0.10) | 0.078 | 3.20 | 16.0256 |
| 2116 | 70:30 | 0.25 (0.175, 0.075) | 0.078 | 3.20 | 16.0256 |

When menthol and menthyl acetate combinations are used in a ratio of 0.8 to 3.20 with Clotrimazole the enhancement of activity of 4 to 16 folds is observed compared to the use of Clotrimazole alone.

Similarly in the synergistic combinations of menthol, menthyl acetate and Clotrimazole, the ratio of menthol to Clotrimazole vary from 0.16 to 2.243 and menthyl acetate to Clotrimazole ratio vary from 0.64 to 1.6.

Ratios of menthol and menthyl acetate used for Amphotericin are mentioned in Table 5.

TABLE 5

| Ratios | Menthol (g): Menthyl acetate (ml) | Amount of the combinations to be used (μg/ml), (menthol, menthyl acetate(μg/ml)) | Amount of Amphotericin B (μg/ml) | Ratio of menthol and menthyl acetate combination to Amphotericin B | Fold enhancement |
|---|---|---|---|---|---|
| 2111 | 20:80 | 0.25 (0.05:0.20) | 1.25 | 0.20 | 2.0 |
| 2112 | 30:70 | 0.25 (0.075, 0.175) | 0.625 | 0.40 | 4.0 |
| 2113 | 40:60 | 0.25 (0.10, 0.15) | 1.25 | 0.20 | 2.0 |
| 2114 | 50:50 | 0.25 (0.125, 0.125) | 0.15625 | 1.60 | 16.0 |
| 2115 | 60:40 | 0.25 (0.15, 0.10) | 0.15625 | 1.60 | 16.0 |
| 2116 | 70:30 | 0.25 (0.175, 0.075) | 0.15625 | 1.60 | 16.0 |

When menthol and menthyl acetate combinations are used at a ratio of 0.20 to 1.60 with Amphotericin B the enhancement of activity of 2 to 16 folds is observed compared to the use of Amphotericin B alone.

Similarly, in the synergistic combinations of menthol, menthyl acetate and Amphotericin B, the ratio of menthol to Amphotericin B vary from 0.04 to 1.12 and menthyl acetate to Amphotericin B ratio vary from 0.12 to 0.64.

Ratios of menthol and menthyl acetate to be used with Nystatin are provided in Table 6.

TABLE 6

| Ratios | Menthol (g): Menthyl acetate (g) | Amount of the combinations to be used (μg/ml), (menthol, menthyl acetate(μg/ml)) | Amount of Nystatin (μg/ml) | Ratio of menthol and menthyl acetate combination to Nystatin | Fold enhancement |
|---|---|---|---|---|---|
| 2111 | 20:80 | 0.25 (0.05:0.20) | 5.0 | 0.05 | 1.0 |
| 2112 | 30:70 | 0.25 (0.075, 0.175) | 0.15625 | 1.6 | 32.0 |
| 2113 | 40:60 | 0.25 (0.10, 0.15) | 1.25 | 0.2 | 4.0 |
| 2114 | 50:50 | 0.25 (0.125, 0.125) | 0.15625 | 1.6 | 32.0 |
| 2115 | 60:40 | 0.25 (0.15, 0.10) | 0.625 | 0.4 | 8.0 |
| 2116 | 70:30 | 0.25 (0.175, 0.075) | 0.3125 | 0.8 | 16.0 |

When menthol and menthyl acetate combinations are used at a ratio of 0.05 to 1.60 with Nystatin the enhancement of activity of 1 to 32 folds is observed compared to the use of Nystatin alone.

Similarly, in the synergistic combinations of menthol, menthyl acetate and Nystatin, the ratio of menthol to Nystatin varies from 0.01 to 0.8 and menthyl acetate to Nystatin ratio varies from 0.04 to 1.12.

The concentration (0.25 μg/ml) used is much below the MIC of different combinations and when the components of the combinations (menthol and menthyl acetate) are used in the proportional concentration neither killing, when used alone, nor facilitating activity when used in combination with the antifungal drug is detected. But when the combinations 2111 to 2116 are used with the antifungal compounds in the ratio 0.05 to 3.2 (combinations: antifungal compound) an increase in activity up to 32 folds is observed. This is definitely the synergistic effect as both the antifungal compound and the combinations (menthol and menthyl acetate) are used much below the level of MIC and as described in the text the components of the combinations menthol and menthyl acetate do not have any activity at the concentrations used in this invention.

ADVANTAGES

1. This phenomena of the enhancement of the antifungal activity by the essential oil components at a very low concentration and specific ratios can revolutionize antifungal consumption and reduce the drug price in the market.
2. Toxicity of the antifungal drugs is reduced to the accepted levels of dosage.
3. Enlargement of antimicrobial spectrum of the drug.
4. Prevention of drug resistance.
5. A very low concentration of essential oil content.

What is claimed is:

1. A method of treating fungal infection comprising administering an effective amount of a bioactive synergistic formulation which consists essentially of:

(a) Menthol in the range of 1–54%;
    (b) Menthyl acetate in the range of 1.5–62%; and
    (c) an antifungal compound in the range of 23–95%.

2. A method according to claim 1 wherein the concentration of antifungal compound is in the range of 0.078–5.0 μg/ml.

3. A method according to claim 1 wherein the antifungal compound is selected from the group consisting of Clotrimazole, Amphotericin B and Nystatin.

4. A method according to claim 3 wherein the concentration of Clotrimazole in the formulation is in the range of 0.078–0.3125 μg/ml.

5. A method according to claim 3 wherein the concentration of Amphoterecin B in the formulation is in the range of 0.15625–1.25 μg/ml.

6. A method according to claim 3 wherein the concentration of Nystatin in the formulation is in the range of 0.15625–5 μ/ml.

7. A method according to claim 3 wherein the ratio of menthol and menthyl acetate with Clotrimazole is in the range of 0.80–3.2.

8. A method according to claim 3 wherein the ratio of menthol and menthyl acetate with Amphotericin is in the range of 0.20–1.6.

9. A method according to claim 3 wherein the ratio of menthol and menthyl acetate with Nystatin is in the range of 0.05–1.6.

10. A method according to claim 1 wherein the concentration of each of Menthol and Menthyl acetate in the formulation is 0.125 μg/ml.

11. A method according to claim 1 wherein the ratio of menthol and menthyl acetate is in the range of 0.05–3.2.

12. A method according to claim 1 wherein the enhanced activity of the formulation is in the range 16 to 32 fold over the antifungal agents used in isolation.

13. A method according to claim 1 wherein the formulation is used to treat human beings.

14. A method according to claim 1 wherein the formulation is effective against pathogens selected from the group consisting of cryptococcus neoformans, candida, and dermatophyte.

15. A method according to claim 14 wherein the formulation is effective against the pathogen *Candida albicans*.

16. A method according to claim 14 wherein the formulation is effective against the pathogen *Cryptococcus neoformans*.

17. A method according to claim 14 wherein the fungal infections treated are Candidiasis, Cryptococcsis, and Dermatophytosis.

18. A method according to claim 1 wherein the formulation is administered in the form of oral, topical preparations and other pharmaceutically accepted methods.

* * * * *